(12) United States Patent
Burke

(10) Patent No.: US 7,807,202 B2
(45) Date of Patent: Oct. 5, 2010

(54) COMPOSITIONS FOR TREATMENT OF VIRAL-INDUCED SKIN LESIONS AND METHODS OF USING SAME

(76) Inventor: Briant Burke, 340 E. Old Saybrook, Boise, ID (US) 83706

( * ) Notice: Subject to any disclaimer, the term of this patent is extended or adjusted under 35 U.S.C. 154(b) by 22 days.

(21) Appl. No.: 11/983,522

(22) Filed: Nov. 9, 2007

(65) Prior Publication Data

US 2008/0131524 A1    Jun. 5, 2008

Related U.S. Application Data

(62) Division of application No. 10/877,474, filed on Jun. 25, 2004, now Pat. No. 7,311,928.

(60) Provisional application No. 60/527,832, filed on Dec. 9, 2003.

(51) Int. Cl.
*A61K 36/00* (2006.01)

(52) U.S. Cl. .................................................. 424/725

(58) Field of Classification Search ........................ None
See application file for complete search history.

(56) References Cited

U.S. PATENT DOCUMENTS

| | | | | |
|---|---|---|---|---|
| 3,551,554 | A | * | 12/1970 | Herschler .................... 424/9.4 |
| 4,497,842 | A | * | 2/1985 | Ehrlich et al. ................ 426/592 |
| 4,595,591 | A | | 6/1986 | Mardi et al. |
| 5,009,890 | A | | 4/1991 | DiPippo |
| 5,073,630 | A | | 12/1991 | Nunes et al. |
| 5,126,376 | A | | 6/1992 | Herman |
| 5,223,271 | A | | 6/1993 | Horrobin |
| 5,286,488 | A | | 2/1994 | Manikas et al. |
| 5,332,215 | A | | 7/1994 | Gonzales |
| 5,541,058 | A | | 7/1996 | Kreider et al. |
| 5,562,900 | A | | 10/1996 | Boyer et al. |
| 5,840,711 | A | | 11/1998 | Gallicchio |
| 5,895,786 | A | * | 4/1999 | Ben-Hur et al. ............. 514/561 |
| 5,945,116 | A | | 8/1999 | Haque et al. |
| 6,043,347 | A | | 3/2000 | Gelder |
| 6,159,977 | A | | 12/2000 | Reeves |
| 6,168,794 | B1 | | 1/2001 | Reusser et al. |
| 6,258,599 | B1 | | 7/2001 | Gelder |
| 6,328,991 | B1 | | 12/2001 | Myhling |
| 6,335,017 | B1 | | 1/2002 | Gelder |
| 6,436,379 | B1 | | 8/2002 | Hill et al. |

(Continued)

OTHER PUBLICATIONS

Brewer, S, MD. : The Right Mixture at the Right Time?; Daily Telegraph, London, England, May 3, 2002, p. 25 (pp. 1-3 of Napralert database print-out).*

(Continued)

*Primary Examiner*—Patricia Leith
(74) *Attorney, Agent, or Firm*—Judy M. Mohr; King & Spalding LLP

(57) ABSTRACT

A composition and method for treatment of viral-induced skin lesions, such as warts, are described. The composition is comprised of tea tree oil and/or derivatives from tea tree oil and one or more minerals, such as iodide and/or selenium. The composition is used to prepare medicaments for the treatment of viral-induced lesions, such as warts caused by the *Molluscum contagiosum* virus, human papillomavirus, and/or herpes simplex virus. The composition is applied topically to the human epidermis and/or to the genital tract as needed.

1 Claim, 2 Drawing Sheets

* P<0.001 compared to vehicle

U.S. PATENT DOCUMENTS

| | | |
|---|---|---|
| 6,500,808 B2 | 12/2002 | Killam |
| 6,921,529 B2 | 7/2005 | Maley |
| 2001/0051169 A1 | 12/2001 | Saint-Leger |

OTHER PUBLICATIONS

Scott, P.M. : Curettage for Molluscum contagiosum; JAAPA, Jun. 2002 (15), 6 pp. 53-54.*

Beck, M.A., et al., "Selenium deficiency increases the pathology of an influenza virus infection", *FASEB Journal*, 15(8):1481-1483 (2001).

Beck, M.A., et al., "Selenium deficiency and viral infection", *J Nutr.*, 133 (5 Supp. 1):1463S-1467S (2003).

Carson, C.F., et al., "Melaleuca alternifolia (tea tree) oil gel (6%) for the treatment of recurrent herpes labialis", *Journal of Antimicrobial Chemotherapy*, 48(3):450-451 (2001).

Carson, C.F. and Riley, T.V., "A review Antimicrobial activity of the essential oil of *Melaleuca alternifolia*"; *Letters in Appl Microbiology*, 16:49-55 (1993).

Carson, C.F. and Riley, T.V., "Antimicrobial activity of the major components of the essential oil of Melaleuca alternifolia", *Journal of Applied Bacteriology*, 78(3):264-269 (1995).

Carson, C.F., et al., "Susceptibility of methicillin-resistant Staphylodoccus aureus to the essential oil of Melaleuca alternifolia", *Journal of Antimicrobial Chemotherapy*, 35:421-424 (1995).

Carson, C.F., et al., "In-vitro activity of the essential oil of Melaleuca alternifolia against Streptococcus spp.", *Journal of Antimicrobial Chemotherapy*, 37(6):1177-1179 (1996).

Elsom, G. and Hide, D., "Susceptibility of methicillin-resistant Staphylococcus aureus to tea tree oil and mupirocin", *Journal of Antimicrobial Chemothethpy*, 43(3):427-428 (1999).

Food Data Chart: Selenium; URL ,http://www.healthyeatingclub.com/info/books-phds/books/foodfacts/thml/data/data50.html> accessed Apr. 30, 2007, 2pages (2007).

Nelson, R.R.S., "In-vitro activities of five plant essential oils against methicillin-resistant Staphylococcus aureus and vancomycin-resistant Enterococcus faecium", *Journal of Antimicrobial Chemotherapy*, 40:305-306 (1997).

Pena, E.F., "Melaleuca alternifolia oil. Its use for trichomonal vaginitis and other vaginal infections", *Ob Gyn.*, 19(6):793-795 (1962).

Penfold, A.R. and Morrison, F.R., "Tea Tree Oils", *The Essential Oils* by Ernest Guenther, vol. IV, D. Van Norstrand Co., Inc., New York, pp. 60-72 (1950).

Schnitzler, P., et al., "Antiviral activity of Australian tea tree oil and eucalyptus oil against herpes simplex virus in cell culture", *Pharmazie*, 56:343-347 (2001).

\* cited by examiner

COMPOSITIONS FOR TREATMENT OF VIRAL-INDUCED SKIN LESIONS AND METHODS OF USING SAME

This application is a divisional of U.S. application Ser. No. 10/877,474, now U.S. Pat. No. 7,311,928 which claims priority to U.S. Provisional Application No. 60/527,832, filed Dec. 9, 2003, now expired, both of which are incorporated herein by reference in their entirety.

FIELD OF THE INVENTION

The present invention relates to compositions for treatment of viral-induced skin lesions, such as warts and tumors. More particularly, the invention relates to a composition for topical application to a skin lesion, the composition comprised of tea tree oil and one or more trace minerals.

BACKGROUND OF THE INVENTION

Skin lesions, such as warts and benign tumors, are very common in humans and often virally-induced. There are a variety of double stranded DNA (dsDNA) viruses that are the cause of skin lesions, each virus being related to a specific clinical presentation. Among the dsDNA wart-causing viruses are the herpesviridae (30 types), papillomaviridae (107 types), and the poxviridae (17 types). Viruses also induce tumors in mammals, for example, many of the known types of human papillomaviruses (HPV). Some of these HPV's have been associated with benign tumors, such as common warts, while others have been implicated as etiologic agents in dysplasia and carcinomas in the oral and genital mucosa.

Viral-induced warts are typically infectious and can be auto inoculated and spread to other individuals by direct contact. Numerous types of warts are observed in humans, including verrucae warts, plantar warts, flat warts, and genital warts. Verrucae warts have a rough surface, are lumpy, and typically flesh colored. Finger-like projections and sometimes dark specks are present, which are the result of thrombosed capillaries. Plantar warts are found on the planter surface of the feet and can be deep and painful. These warts occur singularly, in clusters or can be spread over a wide area. Flat warts are typically small, flat-topped, flesh colored papules that occur primarily on the face, hands, and forearms. Usually the surface of the wart is smooth and they may appear in the hundreds. Genital warts are soft, flesh colored or slightly pigmented, occur in the genitalia of the mammal, and are sexually transmitted. Chronic infections with the viruses that cause genital warts in women are a serious problem as intra epithelial neoplasia or squamous cell carcinoma may develop. See Oski et al., Princ. Pract. Pediatrics, 2nd Ed., pp. 789-790, Lippincott Williams & Wilkins (1994).

Another example of a viral-induced skin lesion are the lesions caused by *Molluscum contagiosum* (MC). MC virus is a member of the poxvirus group. It is a large dsDNA virus that replicates in the cytoplasm of infected cells. Skin lesions caused by MC have an incidence of approximately 1/200 children by the age of 10 in the United States. While the disease may be epidemic in children, it occurs in people of all ages and is worldwide in distribution. In adults, the infection may be spread by sexual contact. Skin lesions caused by MC are characterized by the appearance on the body surface of small, discreet, lobulated epidermal outgrowths or lesions that occur throughout the body. These lesions, which are the result of excessive cellular proliferation stimulated in the keratinocyte layer by virus that has entered through the skin, are discrete pearly white or flesh colored papules that may persist for up to three years. The lesions may have a central pore, which contains within its center dead skin cells and numerous virus particles.

Infections caused by MC commonly last for 9-18 months but the condition can in certain cases persist for as long as 3-4 years. During this time, new crops of lesions appear, each lesion growing slowly for 6-12 weeks and persisting for an average of 3-4 months.

At present there is no drug treatment for MC; the virus is resistant to the commonly used anti-viral agents which are effective in treating other viral infections and the disease is treated only by surgical removal of the lesions, e.g. cryotherapy, or tissue destruction by chemical or physical means. This can be painful and distressing, particularly for children, and does not prevent the reappearance of fresh lesions.

Recently, it has also been observed that individuals with depressed immune systems, such as sufferers of Acquired Immune Deficiency Syndrome (AIDS), are prone to *Molluscum contagiosum* and HPV viral skin infections that can result in tumor growth recalcitrant to treatment, resulting in mental and physical distress to the afflicted individual (Tyring S. K., *Am J Obstet Gynecol.* 189 (3 Suppl):S12-6 (2003)).

Skin lesions are presently treated by various therapies, but none are considered truly effective as they typically fail to totally cure the lesions and do not prevent recurrence. A discussion of presently accepted therapies can be found in Stone, *Cl. Infec. Diseases*, Suppl. 20:991-997 (1995) and in Sterling, *Practioner*, 239(1546):44-47 (1995). One product presently marketed for wart removal is the salicylic acid topical product sold under the tradename OCCLUSAL®-HP, marketed by the GenDerm Corporation of Lincolnshire, Ill. This product is a 17% solution of salicylic acid in a polyacrylic vehicle. Another wart removal product sold under the tradename DUO FILM®, by the Shering-Plough Company of Memphis, Tenn. is a patch containing 40% salicylic acid. The product literature recommends that the wart be washed and dried prior to the application of a medicated patch. This patch is then covered with an additional bandage and the procedure is repeated every 48 hours until the wart is gone, which sometimes takes up to 12 weeks.

More generally, these and other current modalities for the treatment of viral-induced tumors and warts depend on tissue destruction or the removal of the tumor or wart by either: (1) surgical intervention (laser or operative); (2) the application of organic acids, such as glacial acetic acid and/or salicylic acid and lactic acid to "burn" the tumor away; (3) the use of a drug such as podophyllin, interferon, and fluorouracil or 5-fluorouracil; and/or (5) freezing. While being useful for removing the viral-induced growth, these treatment modalities still suffer from one or more of the following drawbacks: (1) they can result in the destruction of healthy uninfected tissue; (2) they can result in scarring and disfigurement; (3) they can result in discomfort to the person being treated thereby; (4) they can result in necrosis of the tumor and the surrounding tissue that can result in a secondary infection requiring treatment with an antibiotic; and (5) they do not result in the destruction of latent viral DNA which may be maintained in surrounding tissues. Furthermore with these conventional treatments, subjects suffer from significant local, and at times, systemic side effects, incomplete resolution, and frequent recurrences and of course, a monetary expense for continued treatment.

SUMMARY OF THE INVENTION

Accordingly, it is an object of the invention to provide a composition for use in treating viral-induced skin lesions in human subjects.

It is a further object of the invention to provide a composition for use in treating viral-induced skin lesions in humans, where the composition does not destroy healthy, uninfected tissues nor result in either significant systemic side effects, local side effects such as initiation, necrosis of tissue surrounding the wart, allergic rashes, scarring, disfigurement, or discomfort to the human treated therewith.

In one aspect, the invention includes a method for treating viral-induced skin lesions in a human subject, comprising administering via topical application to the lesions a composition which comprises a mixture of tea tree oil and at least one mineral.

In one embodiment, the method comprises administering a composition comprising a mixture of tea tree oil and iodine.

In another embodiment, the method comprises administering a composition further comprising selenium.

In another embodiment, the method finds use in treating lesions resulting from infection with a virus in the families selected from the group consisting of herpesviridae, papillomaviridae, and poxviridae. Exemplary virion include *Molluscum contagiosum* and human papillomavirus.

The treatment method, in another embodiment, is for treatment of lesions selected from the group consisting of verrucae warts, plantar warts, flat warts, genital warts, and herpetic lesions.

In yet another embodiment, the method involves administering a composition further comprising dimethyl sulfoxide. The dimethyl sulfoxide is included, in one embodiment, in an amount between 0.0001 Molar to 4.5 Molar.

Selenium, when present in the composition for use in the method, can be present as selenium ion in a range of between 0.01 mM to 200 mM selenium ion, more preferably between 1.0 mM to 100 mM selenium ion.

Iodine is typically present in the composition for use in the method, in an amount between 0.01 mM to 56 mM, preferably between 0.1 mM to 19 mM iodide ion.

In one preferred embodiment, the treatment method is for use in treating viral-induced tumors caused by human papillomavirus (HPV). In another preferred embodiment, the treatment method is for use in treating lesions resulting from the DNA poxvirus *Molluscum contagiosum*.

In still another embodiment, the treatment method is employed for treating genital warts in the female genital tract or on the male external genitalia.

In another aspect, the invention includes a composition, comprising tea tree oil and iodine.

In one embodiment, the composition further comprises selenium.

In yet another embodiment, the composition comprised of tea tree oil and iodine are formulated for topical application. Exemplary formulations include, but are not limited to, an emulsion, a cream, an ointment, a gel, a lotion, a spray, and a soap. The formulation can also take the form of a bandage.

In still another embodiment, the composition further comprises a skin penetration enhancer. A preferred enhancer is dimethylsulfoxide.

The iodine is present in the composition, in one embodiment, in an amount between 0.01 mM to 56 mM, more preferably between 0.1 mM to 19 mM.

The selenium, when present in the composition, is provided in an amount to yield a selenium/iodine molar ratio of between about 0.01-1000, preferably between about 0.1-50, more preferably between about 0.1-20, and still more preferably between about 0.5-20.

In yet another aspect, the invention includes a method of treating a skin lesion induced by a poxviridae, comprising providing a composition comprised of tea tree oil and iodine, as described above.

In one embodiment, the method is for treating a skin lesion induced by the poxviridae *Molluscum contagiosum*. In other embodiments, the method is for treating a skin lesion induced by poxviridae that is recurrent *Varicella-Zoster*, commonly known as shingles, or as acute *Varicella-Zoster*, commonly known as chicken pox.

These and other objects and features of the invention will be more fully appreciated when the following detailed description of the invention is read in conjunction with the accompanying drawings.

DETAILED DESCRIPTION OF THE INVENTION

I. Definitions

Figure 1:
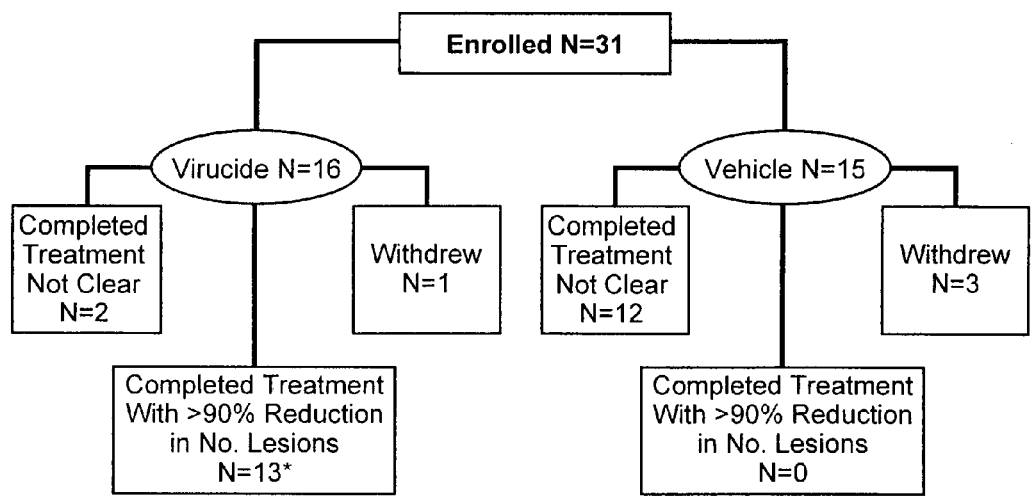
FIG. 1 is a flow chart of a study protocol for treatment of 31 children infected with *Molluscum contagiosum* and enrolled for treatment with a topical preparation comprised of tea tree oil, selenium, and iodine.

As used herein, the term "tea tree oil" intends: (1) the actual essential oil of the species *Melaleuca alternifolia* conforming to Standards Association of Australia (SAA) AS 2782-1985, and/or (2) the active component or components derived from said tea tree oil, and the term "tea tree oil emulsion" shall mean (1) or (2) to which has been emulsified iodine and/or selenium by use of any suitable emulsifying agent, such as dimethylsulfoxide, but not limited to that emulsifying agent. The term "tea tree oil emulsion" is meant to include selenium and/or iodine emulsified with the whole essential oil and any active component or components that are isolated therefrom.

II. Compositions for Treatment

In one aspect, the invention provides a composition comprised of tea tree oil and one or more minerals. In this section, the composition components are described and preparation of the composition is detailed.

A. Composition Components

The composition in accord with the invention is comprised of tea tree oil. Tea tree oil is a pale yellow, somewhat viscous, aromatic liquid obtained from a tree indigenous to swampy regions in certain regions of Australia, *Melaleuca alternifolia*. The steam distillate of the leaves yields an essential oil, tea tree oil, that is used chiefly in the food additive and cosmetic industries. The whole oil is purported to have fungicidal activity (Wenninger J. et al., *J. Assoc. Off. Anal. Chem.*, 53:949 (1970); Moshonas M. G. et al. *Flavour Ind.*, 1:375 (1970)) and antibacterial activity (Belaiche, P., *Phytother.*, 15:13 (1985); Schnitzler, P., *Pharmazie*, 56:343

(2001)). However, there are no reports in the literature of whether or not tea tree oil would act as an effective antiviral agent in vivo for skin lesions.

The chemical composition of tea tree oil is well characterized in the literature, and Table I sets forth the hydrocarbon compounds of whole tea tree oil from *Melaleuca alternifolia* conforming to Standards Association of Australia (SAA) AS 2782-1985 as determined by gas chromatography (Yukawa, Y. et al., SPECTRAL ATLAS OF TERPENES AND THE RELATED COMPOUNDS, Hirokawa Publishing Co., Tokoyo, 1973). Common names of the compounds are listed, followed by the Chemical Abstract Society (CAS) Registry Number, the molecular formula, and percent of area under the integration curve of the gas chromatogram of whole oil.

TABLE 1

Compounds in Whole Tea Tree Oil by Gas Chromatography

| Compound | CAS No. | % AUC of gas chromatogram |
| --- | --- | --- |
| alpha-pinene | 80-56-8 | 2.8% |
| camphene | 79-92-5 | trace % |
| beta-pinene | 127-91-3 | 0.59% |
| sabinene | 3387-41-5 | 0.12% |
| myrcene | 123-35-3 | 0.52% |
| a-phellandrene | 99-83-2 | 0.11% |
| alpha-terpinene | 99-86-5 | 2.74% |
| limonene | 138-86-3 | 3.09% |
| g-terpinene | 99-85-4 | 1.54% |
| terpinolene | 586-62-9 | 2.36% |
| cymene | 99-87-6 | 11.42% |
| dehydro p-cymene | 1195-32-0 | 0.07% |
| cadinene | 29350-73-0 | 1.49% |
| a-cubebene | 11012-64-9 | 0.04% |
| a-copaene | 3856-25-5 | 0.10% |
| a-gurjunene | 73464-47-8 | 0.23% |
| beta-elemene | 33880-83-0 | trace % |
| caryophyllene | 87-44-5 | trace % |
| beta-humulene | 116-04-1 | trace % |
| gamma-muurolene | 10208-80-7 | trace % |
| viridiflorene | 551-57-5 | 1.03% |
| ol-muurolene | 473-13-2 | 0.12% |
| calamenene | 483-77-2 | 0.10% |
| 1,8-cineole | 470-82-6 | 16.50% |
| piperitone | 89-81-6 | 0.08% |
| linalool | 78-70-6 | 0.10% |
| 1-terpineol | 8000-41-7 | trace % |
| 1-terpinen-4-ol | 562-74-3 | 29.41% |
| aromadendrene | 480-20-62 | 2.35% |
| beta-Terpineol | 138-87-4 | 0.24% |
| alloaromadendrene | 552-58-9 | 0.45% |
| alpha-terpineol | 98-55-5 | 3.61% |
| piperitol | 491-04-3 | 0.07% |
| p-cymen-8-ol | 1197-01-9 | 0.13% |

As Table 1 shows, tea tree oil is comprised of a number of components. The gas chromatographic analysis of tea tree oil shows 45 peaks grouped into three principal fractions: hydrocarbons, terpene alcohols, and nonalcoholic oxygenated components. The composition of the invention can include either the whole oil or one or more of the individual components having anti-viral activity. It is contemplated that certain combinations of more ore more of the individual components of tea tree oil can form combinations having therapeutic activity against human viral-induced warts. The data in Table 1 also shows that no salicylic acid, a known agent for the treatment of warts, is present in tea tree oil.

While the biocidal effects of tea tree oil are documented in the medical literature, these effects are almost exclusively antibacterial (Belaiche, P. *Phytother.*, 15:13 (1985); Tong, M. M. et al., *Austr. J. Derm.*, 33:145 (1992); Bassett, I. B. et al., *Med. J. Austr.*, 153:455 (1990); Elsom, G., *J. Antimicrob Chemother,* 43:427 (1999); Carson, C. F. et al., *J. Antimicrob Chemother,* 35:421 (1995)). One study has shown antiviral activity against human herpes virus type II in culture (Schnitzler, P. et al., *Pharmazie,* 56(4):343 (2001)), but this has not been validated clinically. Clinicians recognize that an effect in cell culture can not be extrapolated to a useful clinical effect in humans. Moreover, it is not known from this study if tea tree oil would be an effective therapy for lesions caused by *Molluscum contagiosum* , since a positive effect on one viral infection cannot readily be extrapolated to a prediction of a similar effect on another. For example, acyclovir, the most clinically effective drug in treating herpes, has no effect on lesions caused by *Molluscum contagiosum* . Thus, the efficacy of tea tree oil in treating herpes infections provides no expectation of a similar efficacy in treating *Molluscum contagiosum*.

Thus, it will be appreciated that the composition in accord with the invention, for use in preventing and/or treating viral-induced lesions in humans, is comprised of tea tree oil extract or of one or more individual components of tea tree oil extract. The tea tree oil extract is obtained from the actual essential oil of the species *Melaleuca alternifolia* conforming to Standards Association of Australia (SAA) AS 2782-1985.

In addition to tea tree oil, the composition further includes a mineral, either in its elemental state, as an ion, halide, or salt. Minerals include boron, calcium, chloride, chromium, cobalt, copper, fluoride, geraminum, iodine, iron, lithium, magnesium, manganese, molybdenum, phosphorus, potassium, selenium, silver, sodium, sulfur, vanadium, and zinc. Preferred minerals include so-called trace minerals, particularly the trace minerals selected from iron, copper, zinc, manganese, cobalt, iodine, and selenium.

In studies performed in support of the invention, described below, compositions comprising tea tree oil, selenium, and iodine were prepared. Selenium is a trace mineral essential for human health, important in the activity of detoxifying enzymes such as glutathione peroxidase. Many viral genomes encode for selenium containing proteins that act as a brake on viral replication. Epidemiological evidence suggests that viral mutation resulting in increased virulence occurs in geographic regions where selenium deficiency exists in the soil and in the diet of mammals (including humans) living in the region.

Iodine is also an essential mineral in human nutrition, playing a central role in the production of thyroid hormones It is also involved in the bactericidal action of activated white blood cells. As will be demonstrated below, it has been discovered that tea tree oil emulsified with iodine and, optionally, selenium is effective in treating viral-induced lesions in human subjects. Iodine is typically included in the composition in an amount between about 0.01 mmoles/Liter (mM) and about 100 mM, preferably between about 0.1 mM and 19 mM. One preferred embodiment is a composition comprising 5.6 mM iodine and 87 mM selenium.

The composition can additionally include components necessary for formulation of a preparation suitable for administration, discussed in section B below.

B. Preparation of Compositions Comprising Tea Tree Oil

The composition of the invention comprised of tea tree oil and one or more minerals is formulated for topical application to a patient exhibiting one or more skin lesions. Suitable preparations for topical application include, but are not limited to, liquid preparations, with or without viscosity enhancing agents, where the tea tree oil and mineral(s) are combined with a pharmaceutically acceptable carrier; emulsions, both water-in-oil and oil-in-water; ointments, creams, lotions, gels, sprays, salves, sticks, soaps or any other appropriate preparation. Such topical pharmaceutical compositions are formulated by conventional methods well known in the art. Topical patches or bandages containing the tea tree oil and optional minerals are also suitable for use.

Thus, the tea tree oil along with the selected mineral(s), optionally together with other active substances, are formulated with one or more conventional carriers, excipients or formulation aids to form the desired topical preparation. Exemplary suitable compositions include, for example, those disclosed in EP-A-0289204 (Efamol Holdings PLC).

The composition can include any number of additional components such as preservatives, perfumes, colorants, and skin penetration enhancers. Benefits in transdermal uptake of minerals, such as selenium and iodine, and of tea tree oil, and in the solubility of iodine and selenium can be obtained by formulating the ions and tea tree oil with a skin penetration-assisting or emulsifying agent. Suitable skin penetration-assisting agents include dimethylsulphacetamide or more preferably dimethylsulphoxide (DMSO), known for its effectiveness as a skin permeation enhancer, as well as its excellent solvent properties for both water soluble and insoluble substances. It will be appreciated that a skilled person in the art of topical drug delivery or transdermal drug delivery can select from the variety of skin permeation enhancers known in the art. A review of enhancers is provided in, for example, Sinha, V. R. et al., *Drug Dev. Ind. Pharm.,* 26(11):1131 (2000) or Kanikkannan, N., et al., *Curr. Med. Chem.,* 7(6):593 (2000). The skin penetration enhancers described in these review articles are contemplated for use herein.

The precise concentrations of components in the topical compositions of the invention will depend of course on a number of factors including for example, the severity of the condition to be treated, the form of selenium and iodine used, and the physical nature of the pharmaceutical composition. Generally, however an effective selenium concentration in the composition is between about 0.01 mM to about 200 mM selenium ion, preferably between about 1.0 mM to about 100 mM. Generally, an effective iodine concentration in the composition is between about 0.01 mM and about 100 mM, preferably between about 0.1 mM and about 56 mM, still more preferably between about 0.1 mM and 19 mM.

As noted above, addition of selenium to the composition is optional. However, when selenium is present, the molar ratio of selenium ion to iodine ion is preferably from about 0.01-1000 (selenium/iodine), preferably between about 0.1-50, more preferably between about 0.1-20, and still more preferably between about 0.5-20.

The form of iodine and the form of selenium in the present embodiments may be organic or inorganic, and may comprise any number of commercially available preparations, providing the form used delivers the above stated concentrations of elemental selenium and iodine into a pharmaceutically acceptable formulation. The preferred embodiment comprises the use of iodine as supersaturated potassium iodide solution and the use of selenious acid ($H_2SeO_4$) added to 1 part DMSO and 2 parts whole tea tree oil (33% DMSO).

In particular, the tea tree oil itself as emulsion and/or the extracts (active components) of the tea tree oil when mixed as emulsion are used for the preparation of therapeutic compositions for the treatment of viral-induced warts in humans. An exemplary composition is described in Example 1. The tea tree oil composition are topically applied to persons in need of treatment for lesions caused by a virus, as illustrated in the Examples below.

III. Methods of Treatment

In one aspect, the invention includes a method of treating a viral-induced skin lesion. The lesion that results from the virus will vary according to the virus and the clinical presentation that results from the infection. A typical clinical presentation of virally-induced skin lesions are warts and benign tumors. The virus can be a double stranded DNA (dsDNA) virus, single stranded DNA virus, or and RNA virus. Among the dsDNA wart-causing viruses are the herpesviridae (30 types), papillomaviridae (107 types), and the poxviridae (17 types). A common tumor-and wart inducing virus is human papillomaviruses (HPV).

The method is suitable for treatment of numerous types of warts, including but not limited to verrucae warts, plantar warts, flat warts, and genital warts in both men and women. Treatment of skin lesion caused by *Molluscum contagiosum*, a member of the poxvirus group, by the method of the invention is also contemplated. Another member of the poxviridae family is *Varicella-Zoster*, which presents in its recurrent form as lesions commonly known as shingles and in an acute form commonly known as chicken pox.

The viruses specifically identified herein are merely exemplary and not intended to be limiting in any way.

In studies conducted in support of the invention, an exemplary composition was prepared from tea tree oil, selenium, and iodine (Example 1). The preparation was applied topically to lesions on persons infected with *Molluscom contagiosum*. Specific examples are set forth in Examples 2-11, now to be described.

In a first study, described in Example 2, thirty-one children with *Molluscum contagiosum* were enrolled for treatment with the emulsion of tea tree oil, selenium, and iodine (hereinafter "tea tree oil emulsion"). A flow chart of the study protocol is shown in FIG. 1. Briefly, the children were randomized into two treatment groups, Group I treated with the tea tree oil emulsion of Example 1 and Group II treated with a olive oil as a control. The tea tree oil emulsion or the olive oil were applied to each *Molluscum* lesion twice daily for 30 days.

Figure 2A:
FIGS. 2A-2B are photographs of an area on a 4-year old girl infected with *Molluscum contagiosum* before (FIG. 2A) and after treatment (FIG. 2B) with a topical preparation comprised of tea tree oil, selenium, and iodine.
Figure 2B:
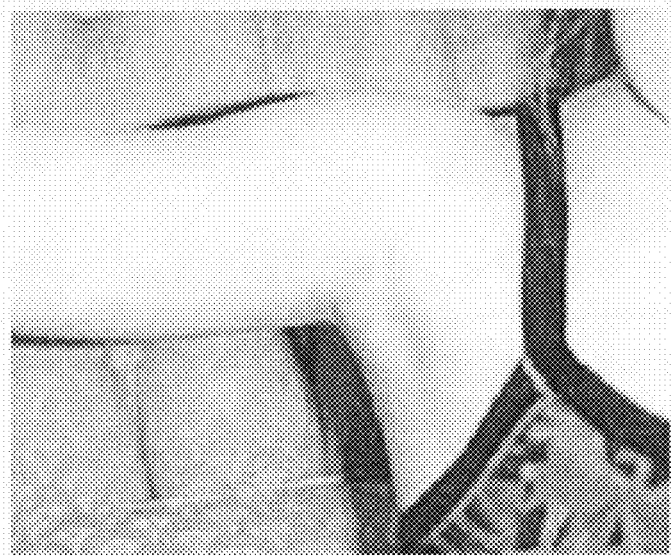

Of the children treated with the tea tree oil emulsion, 81% (13/16) had either complete clearing or a greater than 90% reduction in the number of *Molluscum contagiosum* lesions at the end of 30 days. An additional 2 children had a greater than 50% reduction in *Molluscum* but less than 90% clearance. In the vehicle treated group (Group II), none (0/16) of the children had clearing of the *Molluscum*. In another case study, described in Example 3, a four year old girl presented with severe *Molluscum contagiosum* affecting the axillary areas, arms and chest for over 8 months. The tea tree oil emulsion was applied topically to the affected area twice daily for 2 weeks, after which time the lesions had cleared with only a small amount of residual inflammation. The inflammation continued to clear and after another 2 weeks, no sign of the skin infection remained. Photomicrographs of the affected area are shown in FIGS. 2A-2B, where FIG. 2A shows the affected area before treatment and FIG. 2B shows the same area after treatment. Resolution of the lesions after treatment is readily apparent from the photographs.

Example 4 describes treatment of a two year old boy presented with *Molluscum contagiosum*. The boy had 16 lesions on various parts of the body including the axillae, abdomen, and chest. New lesions had been appearing over the previous two months. Twice daily the tea tree oil emulsion was applied topically and after 6 weeks only 4 lesions were left, after 7 weeks the skin was completely clear.

Examples 5 and 6 describe treatment of two additional children with persistent *Molluscum contagiosum* which had lasted for over a year. Both children were treated by applying directly to the lesions, twice daily, the tea tree oil emulsion prepared according to Example 1. Near complete remission of the lesions was seen after 3 weeks of treatment.

The tea tree emulsion prepared as described in Example 1 was also used to treat an adult female and an adult male, both with sexually transmitted *Molluscum contagiosum*. As described in Examples 7 and 8, conventional treatment of the lesions with the medication sold under the tradename ALDARA™ (1-isobutyl-1H -imidazo[4,5-c]qionolin-4-amine containing cream soly by Riker Laboratories, Inc.) and with Retin-A and cryotherapy were unsuccessful in resolving the lesions. Both adults were treated with a twice daily topical application of the tea tree oil emulsion prepared as described in Example 1. The emulsion successfully resolved the genital *Molluscum contagiosum* lesions.

Example 9 details treatment of an adult female afflicted with human papilloma virus (HPV) genital warts on the labia majorum and pubis. The subject was initially treated with the medication sold under the tradename ALDARA™ (1-isobutyl-1H-imidazo[4,5-c]qionolin-4-amine containing cream soly by Riker Laboratories, Inc.), unsuccessfully. However, three times a day application of the tea tree oil emulsion prepared as described in Example 1 resulted in lesion disappearance after 7 weeks.

Examples 10 and 11 describe treatment of common warts with the tea tree oil emulsion prepared as described in Example 1. Both children presented with warts on their hands, and conventional therapies (cryotherapy and salicylic acid) had failed to eradicate the viral lesions. The tea tree oil emulsion was applied to the lesions three times daily. Shrinkage of the larger warts (4 mm diameter) to less than ⅓ original size, and disappearance of the smaller warts (2 mm diameter or less) was observed after 6 weeks of treatment. After 12 weeks, all warty lesions were gone. During the treatment period, twice a week the warts were gently scrubbed with a stiff nylon bristle brush before application of the tea tree oil emulsion to help remove the dead outer keratinized skin.

These examples show that tea tree oil combined with at least one mineral, and specifically combined with iodine, more specifically combined with iodine and selenium, is effective to resolve virally induced skin lesions. The tea tree oil preparation is preferably applied topically to the lesions and the affected surrounding area at least once daily until the lesions are cleared, typically in between about 2-12 weeks, more preferably in about 2-8 weeks, as illustrated by the working examples above. In some cases, the preparation can be applied twice daily or three times a day.

Accordingly, the present invention provides a method for the treatment of viral-induced skin lesions, namely skin tumors, and more specifically, skin warts. The method involves applying to the lesion and/or the affected surrounding tissue a preparation comprised of tea tree oil and/or derivatives from tea tree oil in combination with at least one mineral, such as iodine or selenium, or both. In preferred embodiments, the tea tree oil preparation is administered for the treatment of lesions caused by the *Molluscum contagiosum* virus, human papillomavirus (HPV), and/or herpes virus (HSV)) in humans. Topical administration of a composition comprising tea tree oil emulsified with iodide and/or selenium in a specific ratio is preferred. Depending on the location of the skin lesions, the composition is applied to the human epidermis and/or to the genital tract.

From the foregoing, it can be seen how various objects and features of the invention are met. Viral-induced tumors, especially of the skin, are very common. These tumors are typically very difficult to treat, control and prevent. The medical community has searched for decades for new therapies to treat this common human malady. The present invention provides a simple and cost-effective method to treat and prevent these viral-induced tumors. The studies disclosed herein illustrate that an emulsion consisting essentially of tea tree oil, selenium, and iodine has specific antiviral properties against the DNA pox virus that causes *Molluscom contagiosum*. The emulsion, when topically applied to the lesions, was effective in the treatment and elimination of *Molluscum contagiosum* warts. Data presented herein also shows that the tea tree oil emulsion was effective against DNA viruses causing genital warts and common warts. The method of treatment neither destroys healthy, uninfected tissue nor results in any local or systemic side effects, scarring, disfigurement or discomfort to the human treated. The method results in the destruction of viral DNA found in the tumor so that instances of incomplete resolution and tumor recurrence are prevented.

IV. EXAMPLES

The following examples further illustrate methods of treatment using the composition described herein and are in no way intended to limit the scope of the invention.

Example 1

Preparation of Exemplary Topical Composition

Tea tree oil was obtained from Coldstream Plantation Pty Ltd Tucabia, Australia. Elemental selenium (as $H_2SeO_3$) and elemental iodine (as KI) were obtained from Spectrum Chemical Supply Co., Garden, Calif. Dimethylsulfoxide was obtained from Spectrum Chemical Supply Co., Garden, Calif.

KI and $H_2SeO_3$ were dissolved in 500 mL dimethyl sulfoxide (DMSO). To this solution was added 1000 mL of tea tree oil. The solution was then thoroughly stirred. Sufficient KI and $H_2SeO_3$ were added to achieve a final concentration of elemental iodine in the solution of 5.6 mM and of elemental selenium of 87 mM.

In the Examples below, the patients were treated twice daily, unless specified otherwise, with this preparation.

Example 2

Children (n=31) with *Molluscum contagiosum* were enrolled for treatment with the topical preparation of Example 1. A flow chart of the study protocol is shown in FIG. 1. The children were otherwise healthy. The length of time with molluscum infection in the subjects ranged from 1-15 months.

Children were randomized into two treatment groups, Group I treated with the tea tree emulsion of Example 1 and Group II treated with a control vehicle (olive oil). Treatment consisted of application of one drop of the tea tree oil emulsion or of the control vehicle to each *Molluscum* lesion twice daily for 30 days.

Treatment was considered successful if *Molluscum* lesions completely cleared or were reduced in number by greater than 90%. The mixture was well tolerated, painless, and consistently effective. The regimen of twice daily topical application resulted in high parental satisfaction and compliance rate.

In Group I, those treated with the tea tree oil emulsion, 81% (13/16) of the children had either complete clearing or a greater than 90% reduction in the number of *Molluscum contagiosum* lesions at the end of 30 days. An additional 2 children had a greater than 50% reduction in *Molluscum* but less than 90% clearance. In the vehicle treated group (Group II), none (0/16) of the children had clearing of the Molluscum.

In this study, adverse effects were limited to a small amount of redness around the base of some lesions. No child discontinued treatment due to adverse reactions and no child displayed any sign of pain or discomfort from application of tea tree oil emulsion according to parental report.

Example 3

A four year old girl presented with severe *Molluscum contagiosum* affecting the axillary areas, arms and chest for over 8 months. A composition, prepared as described in Example 1, comprised of a tea tree oil emulsion was applied topically to the affected area twice daily for 2 weeks, after which time the lesions had cleared with only a small amount of residual inflammation. The inflammation continued to clear and after another 2 weeks, no sign of the skin infection remained. The results are shown in FIGS. 2A-2B.

Example 4

A two year old boy presented with *Molluscum contagiosum*. He had 16 lesions on various parts of the body including the axillae, abdomen, and chest. New lesions had been appearing over the previous two months. He was treated twice daily with the topical preparation of tea tree oil, selenium, and iodine, prepared as described in Example 1. After 6 weeks only 4 lesions were left, after 7 weeks the skin was completely clear.

Example 5

A seven year old girl with persistent *Molluscum contagiosum* which had lasted for over a year presented with 24 lesions. The child was treated by applying directly to the lesions, twice daily, the tea tree oil emulsion prepared according to Example 1. After 3 weeks of treatment, one original lesion remained. New lesions were treated when first observed and were resolving within 1 week of twice daily application of the tea tree oil emulsion.

Example 6

A four year old girl who had had persistent *Molluscum contagiosum* for over a year presented with oozing confluent lesions to the axillary areas. The girl was treated by applying twice daily the tea tree oil emulsion prepared as described in Example 2. The treatment resulted in complete remission after 3 weeks.

Example 7

A 24 year old female with sexually transmitted *Molluscum contagiosum* diagnosed by her private physician had failed treatment with the medication sold under the tradename ALDARA™ (1-isobutyl-1H-imidazo[4,5-c]qionolin-4-amine containing cream soly by Riker Laboratories, Inc.) and Retin-A. After 8 weeks of twice daily topical application of the tea tree oil emulsion prepared as described in Example 1, the genital *Molluscum contagiosum* lesions had resolved. New lesions quickly responded (within 2 weeks) to application.

Example 8

A 34 year old male contracted sexually transmitted *Molluscum contagiosum* that had persisted for 18 months despite repeated painful cryotherapy to the perineum. Twice daily application of the tea tree oil emulsion prepared as described in Example 1 resulted in improvement within 3 weeks and complete resolution of the original lesions within 9 weeks. No further *Molluscum contagiosum* lesions occurred after 1 year of follow-up.

Example 9

A 19 year old female had HPV genital warts diagnosed by her private physician. The lesions were on the labia majorum and pubis. Initial treatment with the medication sold under the tradename ALDARA™ (1-isobutyl-1H-imidazo[4,5-c]qionolin-4-amine containing cream soly by Riker Laboratories, Inc.) was ineffective after 4 months. Three times a day application of the tea tree oil emulsion prepared as described in Example 1 resulted in lesion disappearance after 7 weeks. Application immediately to newly discovered lesions resulted in rapid resolution, generally within 4 weeks.

Example 10

An 11 year old boy presented with common verrucae on the dorsum of both hands involving the metacarpal-phalangeal joints for over 3 years. Cryotherapy had been used multiple times but the warts multiplied and spread after each treatment. Three times daily application of tea tree oil emulsion prepared as described in Example 1 resulted in shrinkage of the larger warts (4 mm diameter) to less than ⅓ original size, and disappearance of the smaller warts (2 mm diameter or less) after 6 weeks of treatment. After 12 weeks, all warty lesions were gone. Twice a week the warts were gently scrubbed with a stiff nylon bristle brush before application of the tea tree oil emulsion to help remove the dead outer keratinized skin.

Example 11

A 9 year old girl presented with common warts affecting the palms of both hands resistant to treatment. Salicyclic acid (15%) had been tried but the warts multiplied and spread. Three times a day application of the tea tree oil emulsion prepared as described in Example 1 to each warty lesion resulted in clearing of the lesions after 12 weeks. Twice weekly gentle scrubbing with a stiff nylon bristle brush before application of the emulsion to help remove the dead outer keratinized skin was performed.

Although the invention has been described with respect to particular embodiments, it will be apparent to those skilled in the art that various changes and modifications can be made without departing from the invention.

It is claimed:

1. A method of treating a skin lesion induced by a human papilloma virus, comprising:
    administering topically to the lesion a composition comprised of pharmaceutically effective amounts of tea tree oil, selenium, and iodine.

* * * * *